US006811707B2

(12) United States Patent
Rovatti et al.

(10) Patent No.: US 6,811,707 B2
(45) Date of Patent: Nov. 2, 2004

(54) DIALYSIS MACHINE AND METHOD OF CHECKING THE FUNCTIONALITY OF A DIALYSIS MACHINE

(75) Inventors: Paolo Rovatti, Modena (IT); Alessandro Vasta, Modena (IT)

(73) Assignee: Gambro Dasco S.p.A., Medolla (IT)

( * ) Notice: Subject to any disclaimer, the term of this patent is extended or adjusted under 35 U.S.C. 154(b) by 198 days.

(21) Appl. No.: 10/148,132

(22) PCT Filed: Sep. 24, 2001

(86) PCT No.: PCT/IB01/01745
§ 371 (c)(1),
(2), (4) Date: May 28, 2002

(87) PCT Pub. No.: WO02/26291
PCT Pub. Date: Apr. 4, 2002

(65) Prior Publication Data
US 2002/0179505 A1 Dec. 5, 2002

(30) Foreign Application Priority Data
Sep. 29, 2000 (IT) ..................... TO2000A0908

(51) Int. Cl.⁷ .............................. B01D 61/32
(52) U.S. Cl. ................. 210/739; 210/85; 210/96.1; 210/96.2; 210/102; 210/134; 210/141; 210/143; 210/321.71; 210/646; 340/517; 340/825.06; 340/825.36
(58) Field of Search ............ 210/85, 96.1, 96.2, 210/102, 134, 141, 143, 321.79, 646, 739, 321.71; 340/500, 506, 517, 825.06, 825.36; 602/FOR 115, FOR 134, FOR 135

(56) References Cited

U.S. PATENT DOCUMENTS

| 4,739,492 A | 4/1988 | Cochran |
| 5,472,614 A | 12/1995 | Rossi |
| 5,620,608 A | 4/1997 | Rosa et al. |
| 5,858,239 A | 1/1999 | Kenley et al. |
| 6,066,261 A | 5/2000 | Spickermann |

FOREIGN PATENT DOCUMENTS

| EP | 0 384 155 | 8/1990 |
| EP | 0432 138 A2 | 6/1991 |

Primary Examiner—John Kim
(74) Attorney, Agent, or Firm—Finnegan, Henderson, Farabow, Garrett & Dunner, L.L.P.

(57) ABSTRACT

A dialysis machine may include a main control unit provided with a memory that stores the parameters of a dialysis treatment carried out on a patient and a plurality of slave control units interacting with the main control unit. The slave control unit may provide the control of the dialysis treatment carried out on the patient. A functionality checking unit may include a memory that stores dialysis treatment parameters and interacts with the main control unit to carry out checking of the functionality of the dialysis machine. At predetermined intervals of time, the functionality checking unit may send the dialysis treatment parameters stored in its memory to the main control unit, and the main control unit may compare the dialysis treatment parameters stored in its memory with those sent from the functionality checking unit, and generate an alarm signal if the dialysis treatment parameters do not coincide with each other.

27 Claims, 2 Drawing Sheets

DIALYSIS MACHINE AND METHOD OF CHECKING THE FUNCTIONALITY OF A DIALYSIS MACHINE

Figure 1:
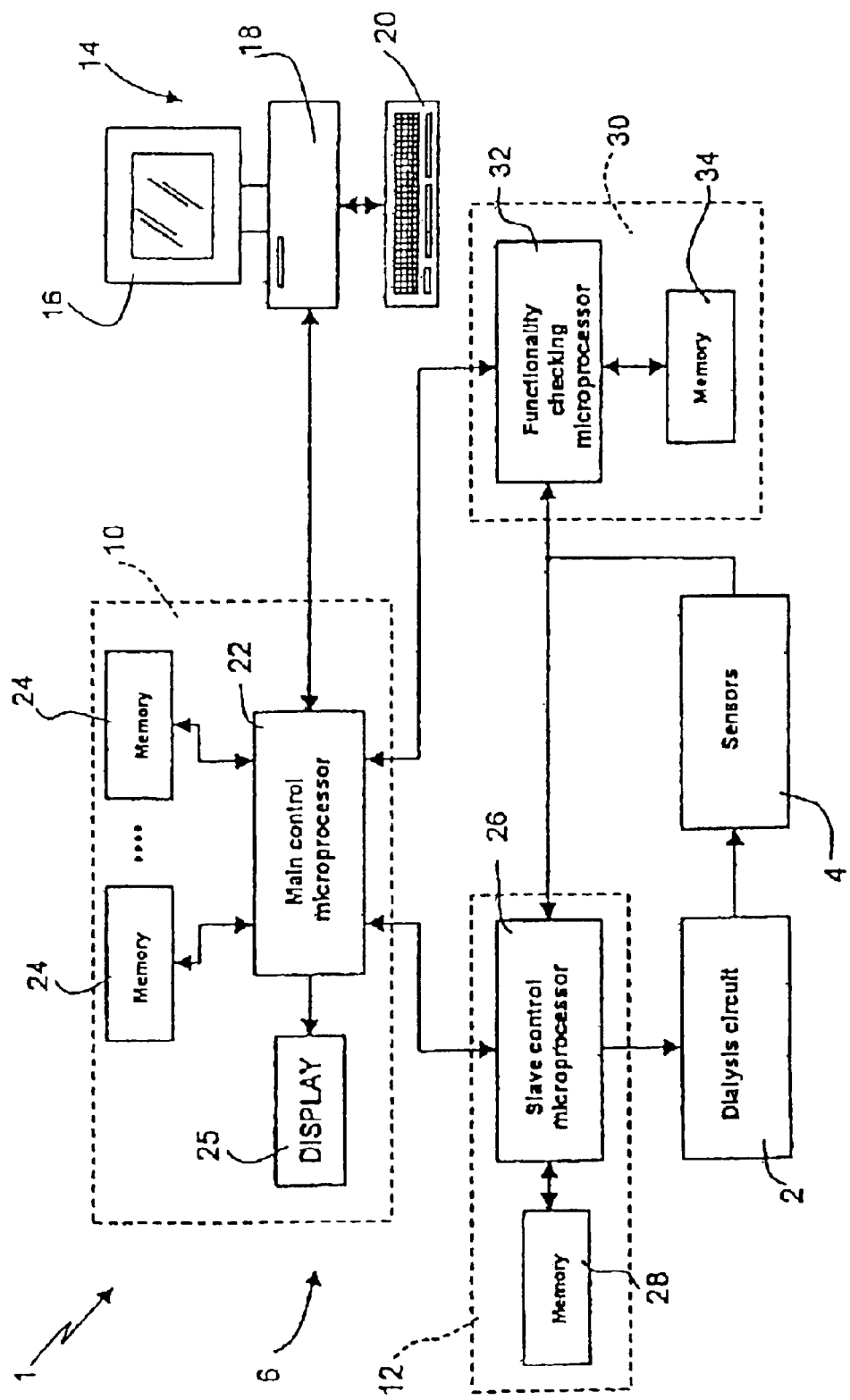

The present invention relates to a dialysis machine and a method of checking the functionality of a dialysis machine.

As is known, in cases of renal insufficiency the patient's blood contains particles of low molecular weight which have to be eliminated by a dialysis treatment carried out by means of a dialysis machine.

In particular, the blood is treated by means of a dialysis filter consisting of a blood chamber and a dialyzing chamber separated by a semi-permeable membrane, through which chambers the blood to be treated and a dialyzing solution, respectively, pass during operation; during the dialysis treatment, the undesired particles in the blood migrate from the blood chamber to the dialyzing chamber through the semi-permeable membrane by both diffusion and convection.

All dialysis machines available on the market at present are provided with more or less sophisticated control devices whose purpose is to regulate the operation of the dialysis machines. In particular, the most sophisticated control devices are designed to implement safety procedures intended, on the one hand, to check that any modification of the dialysis treatment parameters is appropriate for the patient treated by dialysis and is compatible with the current state of the dialysis machine, and, on the other hand, to prevent the incorrect modification of the dialysis treatment parameters which may have harmful effects on the health of the patient treated by dialysis.

However, there are many other situations or conditions of operation of dialysis machines which may have harmful effects on the health of the patient treated by dialysis, and on which the control devices of dialysis machines currently on the market do not carry out any kind of check.

The object of the present invention is to provide a dialysis machine and a method of checking the functionality of a dialysis machine which enable the above problems to be overcome.

According to the present invention, a dialysis machine is provided, comprising main control means provided with memory means which store the parameters of the dialysis treatment carried out on a patient by means of the said dialysis machine; slave control means interacting with the said main control means to provide the control of the dialysis treatment carried out on the patient; and means of checking the functionality provided with memory means which store the dialysis treatment parameters, and interact with the said main control means to carry out the checking of the functionality of the said dialysis machine; the said means of checking the functionality comprising transmission means for sending to the said main control means the dialysis treatment parameters stored in the memory means of means of checking the functionality when predetermined conditions are detected; and in that the said main control means comprise comparison means for comparing with each other the dialysis treatment parameters stored in the memory means of the said means of checking the functionality and the dialysis treatment parameters stored in the memory means of the said main control means, and signal generator means for generating an alarm signal if the said dialysis treatment parameters do not coincide with each other.

The present invention also provides a method of checking the functionality of a dialysis machine comprising main control means provided with memory means which store the parameters of the dialysis treatment carried out on a patient by means of the said dialysis machine; and slave control means interacting with the said main control means for controlling the dialysis treatment carried out on the patient; characterized in that it comprises the steps of:

providing means of checking the functionality, these means being provided with memory means;

storing the said dialysis treatment parameters in the said memory means of the said means of checking the functionality;

when predetermined conditions are detected, comparing the dialysis treatment parameters stored in the memory means of the said means of checking the functionality with the dialysis treatment parameters stored in the memory means of the said main control means; and generating an alarm signal if the said parameters do not coincide with each other.

Figure 2:
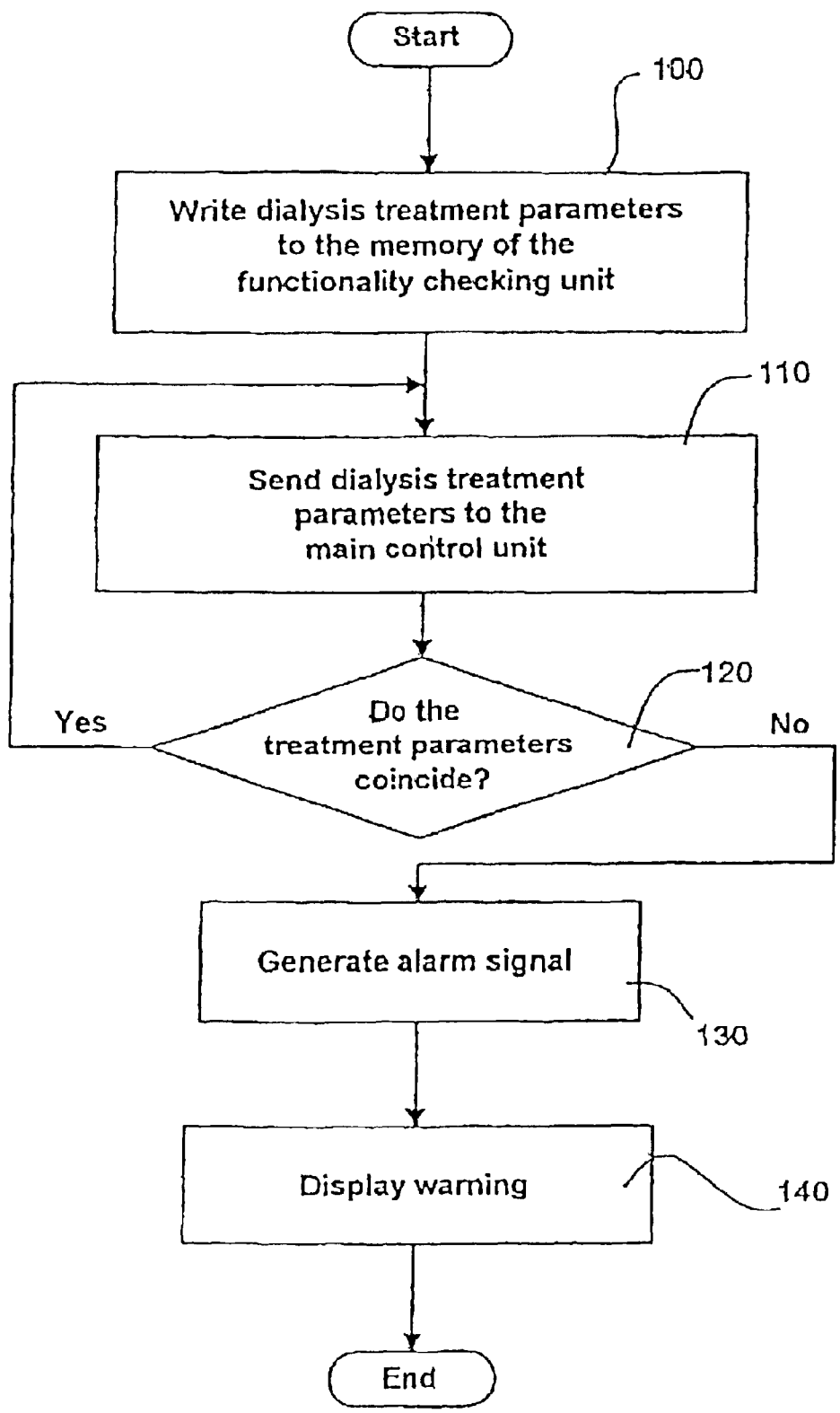

To facilitate the understanding of the present invention, a preferred embodiment will now be described, purely by way of example, without restrictive intent and with reference to the attached drawings, in which:

FIG. 1 shows a schematic block diagram of a dialysis machine made according to the present invention; and FIG. 2 shows a flow diagram of the operations carried out by the dialysis machine of FIG. 1 for the detection of malfunctions of the dialysis machine.

In FIG. 1, the number 1 indicates, as a whole, a dialysis machine made according to the present invention.

The dialysis machine 1 comprises a dialysis circuit, shown schematically as a block indicated by 2, formed by the various parts of the dialysis machine 1 dedicated to the provision of the actual dialysis treatment, such as the artery and vein lines, the dialyzing filter, the blood pumps, the dialyzing liquid pumps, the ultra-filtration pump, etc.; and a plurality of sensors, shown schematically as a single block indicated by 4, located at various points of the dialysis circuit 2 to measure quantities relating to the dialysis treatment, such as the concentration of the dialyzing liquid, the concentration of haemoglobin, the blood volume, the coefficient of ultra-filtration, etc.

The dialysis machine 1 also comprises a control device 6 having a circuit architecture of the "Master-Multislave" type, in other words one of the type comprising main control means including a main (or "master") control unit, indicated by 10, and slave control means including a plurality of "slave" control units, shown schematically as a single block indicated by 12 and dedicated to the control of the operation of specific parts of the dialysis circuit 2 or of specific processes connected with the dialysis treatment, for example the control of the hydraulic circuit, the control of the blood circuit, the control of haemodiafiltration, the control of ultrafiltration, etc.

The dialysis machine also comprises a personal computer 14, provided with a display unit, a processing unit 18 and a keyboard 20, dedicated to the control of all the processes connected with the dialysis treatment of the patient and the actions carried out by the user of the dialysis machine 1, such as requests for information on the state of progress of the dialysis treatment, the setting of the dialysis treatment parameters, etc.

In the main control unit 10 there is installed a multitasking operating system for the implementation of specific procedures, such as procedures connected with the dialysis treatment itself, procedures for the distribution of data and commands, procedures for monitoring the blood circuit, procedures for checking the correctness of all the conditions which can in any way represent a risk for the health of the patient treated by dialysis, procedures for taking actions intended to bring the dialysis machine into a safety condition, procedures for checking modifications of the parameters of the dialysis treatment, etc.

The main control unit 10 essentially comprises a main control microprocessor 22, connected to the processing unit 18 of the personal computer 14 and dedicated to the supervision of the operation of one or more dialysis machines 1 which can be connected in a network, and a plurality of memories 24, connected to the main control microprocessor 22 and virtually separated and operationally independent of each other; these memories being provide redundancy of storage, in order to prevent what is known as a "soft error", and each of these memories storing the dialysis treatment parameters, such as the variation of ultrafiltration during the dialysis session, the variation of the concentration of the dialyzing liquid during the dialysis session, etc.

The multitude of dialysis treatment parameters are at least duplicated; each copy is separated from the other and is stored in a corresponding of the virtually or physically separated memories 24.

The main control unit 10 also comprises a display unit 25, which displays data of various kinds relating both to the dialysis treatment, for example information on the state of progress of the dialysis treatment, parameters of the dialysis treatment, etc., and to the functionality of the dialysis machine.

Each slave control unit 12 comprises a slave control microprocessor 26 and a memory 28 connected to the slave control microprocessor 26. In particular, the slave control microprocessors 26 are connected bi-directionally to the main control microprocessor 22 and receive at their inputs the measurement signals, generated by the sensors 4; the slave control microprocessors 26 receives the measurement signals from the sensors in order to provide the control of the corresponding parts of the dialysis circuit 2 or of the corresponding processes connected with the dialysis treatment to which they are dedicated; the microprocessors achieve their control objectives in a way which is known and is therefore not described in detail, while the memories 28 store the respective parameters of the dialysis treatment or the parameters relating to the operation of the parts of the dialysis circuit for which the corresponding slave control microprocessors 26 provide control.

With reference again to FIG. 1, the main control microprocessor of the main control unit 10 stores a copy the parameters of the dialysis treatment in each of the memories 24 and also sends to the slave control means a further copy of the parameters of the dialysis treatment; more in detail to each slave control microprocessor 26 only a corresponding set of said parameters (one or more) is sent. Each slave control microprocessor is indeed responsible for the control of a corresponding set of the parameters and stores in the respective memory 28 its corresponding set or part of the parameters.

According to the present invention, the control device 6 of the dialysis machine 1 also comprises means of checking the functionality provided with memory means which store a further copy of the dialysis treatment parameters, and interact with the said main control means (10); the means 30 includes another slave unit, denoted hereafter by the term "functionality checking unit" and indicated by 30, which is distinct and physically separated from the main control unit 10 and interacts with the latter, in the way described more fully below, to provide continuous checking of the functionality of the dialysis machine 1 and reliability of the control device 6 in particular.

The functionality checking unit 30 essentially comprises a functionality checking microprocessor 32 and a memory 34 which is connected to the functionality checking microprocessor 32 and which stores the copy of the parameters of the dialysis treatment received by the main control microprocessor. In detail, the functionality checking microprocessor 32 is connected bidirectionally to the main control microprocessor 22, receives at its input both the parameters stored in the main memories and the measurement signals generated by the sensors 4 according to what hereinafter described. It is to be noted that, for each parameter, the corresponding sensor is generally duplicated so that a first sensor for each respective parameter sends its input to the slave control microprocessor 26 and a second sensor detecting the same parameter sends its input to the functionality checking microprocessor 32. In other words for each parameter to be controlled two sensors or two independent sensing sources are generally provided with: one cooperating with the slave control microprocessor 26 and one with the functionality checking microprocessor 32. Note that generally not all the sensors are really duplicated since information related to the variation with time of some parameters can be indirectly determined by the functionality checking microprocessor 32 through other means conventionally present in the dialysis machine.

The operative connection between the main control unit 10 and each slave control unit 12 and the operative connection between the main control unit 10 and the functionality checking unit 30 are so designed that the functionality checking unit receives at its inputs and stores in its memories:

copy of the treatment parameters present in the memories 24 (as above described), the measurements detected by its own sensors or sensing sources, and copy of the measurement signals (via the main control unit 10) acquired by the sensors or sensing sources associated to each slave control unit 12.

Therefore the functionality checking unit has in its memories the parameters of the treatment set by the main unit (i.e. the desired parameters for the dialysis treatment), the measurement of the actual parameters as sensed by the sensing sources directly associated to the functionality checking unit itself and the copy of the measurements of the actual parameters as sensed by the sensing sources associated to each slave control unit 12.

The functionality checking microprocessor 32 performs two functions; the first function is that of acquiring, via the main control microprocessor 22, the measurement signals acquired from the slave control microprocessors 26, and comparing them with its own measurement signals acquired for the purpose of constantly checking the correctness of the operation of the slave microprocessors 26.

The second function is that of interacting with the main control microprocessor 22 to constantly check the correctness of the operation of the dialysis machine 1 and of the memories of the control device 6 too, by implementing the operations described below with reference to the flow diagram of FIG. 2.

In particular, as shown in FIG. 2 and as already mentioned, the main control microprocessor 22 initially writes to the memory 34 of the functionality checking microprocessor 32 a copy of the parameters of the dialysis treatment entered by the operator through the keyboard 20 of the personal computer and stored in a redundant way in the memories 24 of the main control microprocessor 22 (block 100).

Subsequently, at predetermined instants of time, for example after every clock pulses, the functionality checking microprocessor 32 sends a copy of the dialysis treatment parameters stored in its memory 34 to the main control microprocessor 22, which acquires these parameters and stores them in one of its memories 24 (block 110).

The main control microprocessor 22 then compares the copy of the dialysis treatment parameters sent from the functionality checking microprocessor 32 with the original dialysis treatment parameters stored in each of its memories 24 (block 120).

If the dialysis treatment parameters sent from the functionality checking microprocessor 32 coincide with those originally stored in each of the memories of the main control microprocessor 22 (YES output of block 120), the main control microprocessor 22 detects the correct functionality of the dialysis machine 1 and therefore continues to carry out its functions normally, returning to the block 110, whereas, if the dialysis treatment parameters sent from the functionality checking microprocessor 32 do not coincide with the dialysis treatment parameters stored in each of the memories 24 of the main control microprocessor 22 (NO output of block 120), the main control microprocessor 22 detects the presence of a malfunction and generates an alarm signal, displays it on the display unit 25, and sends it to the processing unit 18 of the personal computer 14 (block 130).

The alarm condition is then displayed on the display unit 25, in the form of a text or an icon indicating this malfunction and therefore the fact that the functionality of the dialysis machine 1 and of the slave control units in particular has not been verified (block 140) since the functionality checking microprocessor or its memories might be no longer reliable. In other words according to the above architecture the memories of the main control unit are duplicated to have high reliability of any information stored therein, the operation of the slave units is constantly controlled by the main unit and also by the functionality checking unit (independent from the slave units), and finally the proper working of the memories of the functionality checking units is also periodically monitored by the main unit.

When the alarm signal is received, the processing unit 18 of the personal computer 14 can also cause this alarm condition to be displayed on the display unit 16.

An examination of the characteristics of the dialysis machine 1 made according to the present invention will clearly reveal the advantages that it provides.

In particular, by checking the functionality by means of the checking unit it is possible to virtually eliminate the probability of the appearance in dialysis machines of malfunctions which may damage the health of patients treated by dialysis; in this way, the safety of the dialysis treatment is considerably enhanced. Indeed the functionality checking unit 30 makes sure that the slave control microprocessors are really properly controlling the parameters. Moreover, in case of failure in the functionality checking unit 30, and in its memories in particular, the failure condition is periodically monitored and identified by the main control unit without any risk of an improper and false checking of the slave control units by the functionality checking unit.

Finally, the dialysis machine described and illustrated herein can clearly be modified and varied without departure from the scope of protection of the present invention as defined in the attached claims.

What is claimed is:

1. Dialysis machine, comprising:

main control means provided with memory means which store the parameters of the dialysis treatment carried out on a patient by means of the said dialysis machine;

slave control means interacting with the said main control means to provide the control of the dialysis treatment carried out on the patient; and means of checking the functionality provided with memory means which store the dialysis treatment parameters, and interact with the said main control means to carry out the checking of the functionality of the said dialysis machine, the said means of checking the functionality comprising transmission means for sending to the said main control means the dialysis treatment parameters stored in the memory means of said means of checking the functionality when predetermined conditions are detected;

wherein the said main control means comprise comparison means for comparing with each other the dialysis treatment parameters stored in the memory means of the said means of checking the functionality and the dialysis treatment parameters stored in the memory means of the said main control means, and signal generator means for generating an alarm signal if the said dialysis treatment parameters do not coincide with each other.

2. Dialysis machine, comprising:

main control means provided with memory means which store the parameters of the dialysis treatment carried out on a patient by means of said dialysis machine;

slave control means interacting with the main control means to provide control of a dialysis treatment carried out on a patient; and means of checking the functionality provided with memory means which store a copy of the dialysis treatment parameters, and interact with the said main control means to carry out the checking of the functionality of the said dialysis machine, said means of checking the functionality being capable of sending to said main control means the dialysis treatment parameters stored in the memory means of said means of checking the functionality;

said main control means periodically comparing with each other the dialysis treatment parameters stored in the memory means of the said means of checking the functionality and the dialysis treatment parameters stored in the memory means of the said main control means and being able to cause an alarm signal generation if the dialysis treatment parameters stored in the memory means of the said means of checking the functionality and the dialysis treatment parameters stored in the memory means of the said main control means are different.

3. Dialysis machine according to claim 1, characterized in that the said transmission means send to said main control means the dialysis treatment parameters stored in the memory means of the functionality checking means at predetermined intervals of time.

4. Dialysis machine according to any one of claims 1 and 2, characterized in that it also comprises display means connected to said main control means to display a message indicating a malfunction of the said dialysis machine on receipt of the said alarm signal.

5. Dialysis machine according to claim 1 or claim 2, characterized in that said main control means includes at least a main control microprocessor and in that said memory means includes a plurality of memories connected to the main microprocessor.

6. Dialysis machine according to claim 5, characterized in that said plurality of memories are virtually or physically separated and operationally independent of each other.

7. Dialysis machine according to claim 6, characterized in that the main control microprocessor at least duplicates the multitude of dialysis treatment parameters, each copy of the dialysis treatment parameters is separated from the other and is stored in a corresponding of the virtually or physically separated memories.

8. Dialysis machine according to claim 1 or claim 2, characterized in that the slave control means includes a plurality of slave control units.

9. Dialysis machine according to claim 8, characterized in that each slave control unit comprises a slave control microprocessor and a memory connected to the slave control microprocessor.

10. Dialysis machine according to claim 9, characterized in that it comprises sensors located at various points of the dialysis circuit to measure quantities relating to the dialysis treatment, the slave control microprocessors being connected bi-directionally to a main control microprocessor, for storing in the memories copy of the respective parameters of the dialysis treatment or of the parameters relating to the operation of the parts of the dialysis circuit for which a corresponding one of said slave control microprocessors provides control, the slave control microprocessors also receiving at their inputs the measurement signals generated by the sensors, for providing control of corresponding parts of the dialysis circuit or of the corresponding processes connected with the dialysis treatment to which they are dedicated.

11. Dialysis machine according to claim 9, characterized in that the memories store copy of the respective parameters of the dialysis treatment or of the parameters relating to the operation of the parts of the dialysis circuit for which the corresponding slave control microprocessor provides control.

12. Dialysis machine according to claim 1 or claim 2, characterized in that means of checking the functionality includes a functionality checking unit, which is distinct and physically separate from the main control means 10 and interacts with the latter.

13. Dialysis machine according to claim 12, characterized in that the functionality checking unit comprises a functionality checking microprocessor and a memory which is connected to the functionality checking microprocessor and which stores the copy of the parameters of the dialysis treatment received by the main control microprocessor.

14. Dialysis machine according to claim 13, characterized in that it comprises sensors located at various points of the dialysis circuit to measure quantities relating to the dialysis treatment, the functionality checking microprocessor being connected bi-directionally to the main control microprocessor and receiving at its input both copy of the parameters stored in the memory means and the measurement signals generated by the sensors and being able to compare them for the purpose of constantly checking the correctness of the operation of the slave microprocessors.

15. Dialysis machine according to claim 10, characterized in that, at least for a predetermined number of parameters, the corresponding sensors are duplicated so that a first sensor for each respective parameter sends its input to the slave control microprocessor and a second sensor detecting the same parameter sends its input to the functionality checking microprocessor.

16. Dialysis machine according to claim 14, characterized in that the functionality checking microprocessor, at predetermined instants of time is capable of sending a copy of the dialysis treatment parameters stored in its memory to the main control microprocessor, which acquires these parameters and then compares the copy of the dialysis treatment parameters from the functionality checking microprocessor with the original dialysis treatment parameters stored in each of its memories, the main control microprocessor generating an alarm signal if the dialysis treatment parameters sent from the functionality checking microprocessor do not coincide with the dialysis treatment parameters stored in each of the memories of the main control microprocessor.

17. Dialysis machine according to claim 15 characterized in that the functionality checking unit receives at its inputs and stores in its memories:
   copy of the treatment parameters present in the memories,
   the measurements detected by its own sensors or sensing sources, and
   via the main control unit copy of the measurement signals acquired by the sensors or sensing sources associated to each slave control unit.

18. Method of checking the functionality of a dialysis machine, said dialysis machine including:
   main control means provided with memory means which store the parameters of the dialysis treatment carried out on a patient by means of the said dialysis machine;
   slave control means interacting with the said main control means for controlling the dialysis treatment carried out on the patient; and
   means of checking the functionality provided with memory means;
   said method comprising the following steps
      storing the dialysis treatment parameters in the said memory means of the said means of checking the functionality;
      when predetermined conditions are detected, comparing the dialysis treatment parameters stored in the memory means of the said means of checking the functionality with the dialysis treatment parameters stored in the memory means of the said main control means; and
      generating an alarm signal if the said parameters do not coincide with each other.

19. Method of checking according to claim 18, characterized in that the said step of comparing comprises the step of sending to the said main control means the dialysis treatment parameters stored in the memory means of the said means of checking the functionality when the said predetermined conditions are detected.

20. Method of checking according to claim 18 or 19, characterized in that the said step of comparing is carried out at predetermined intervals of time.

21. Method of checking according to claim 18 or claim 19, characterized in that it also comprises the step of:
   displaying on display means of the said dialysis machine a message indicating a malfunction of the said dialysis machine when the said alarm signal is detected.

22. Method of checking the functionality of a dialysis machine, said dialysis machine including:
   a dialysis circuit;
   a plurality of sensors, located at various points of the dialysis circuit to measure quantities relating to the dialysis treatment;
   main control means provided with memory means which store the parameters of the dialysis treatment to be carried out on a patient by means of the said dialysis machine;
   slave control means interacting with the said main control means for controlling the dialysis treatment carried out on the patient; and means of checking the functionality provided with memory means;

said method comprising the following steps
  storing copy of the dialysis treatment parameters in the said memory means of the said means of checking the functionality;
  at prefixed time intervals, comparing the dialysis treatment parameters stored in the memory means of the said means of checking the functionality with the dialysis treatment parameters stored in the memory means of the said main control means; and
  generating an alarm signal if the said parameters do not coincide with each other.

23. Method of checking the functionality according to claim 22, characterized in that it comprises the following step:
  storing in the memories copy of the respective parameters of the dialysis treatment or of the parameters relating to the operation of the parts of the dialysis circuit for which the corresponding slave control microprocessor provides control, the slave control microprocessor also receiving at their inputs the measurement signals generated by the sensors, for providing control of corresponding parts of the dialysis circuit or of the corresponding processes connected with the dialysis treatment to which they are dedicated.

24. Method of checking the functionality according to claim 22, characterized in that it comprises the following step:
  comparing the measurement signals generated by the sensors and the dialysis treatment parameters in said memory means of said means of checking the functionality for the purpose of constantly checking the correctness of the operation of the slave microprocessors.

25. Dialysis machine according to claim 14, characterized in that, at least for a predetermined number of parameters, the corresponding sensors are duplicated so that a first sensor for each respective parameter sends its input to the slave control microprocessor and a second sensor detecting the same parameter sends its input to the functionality checking microprocessor.

26. Dialysis machine according to claim 25 characterized in that the functionality checking unit receives at its inputs and stores in its memories:
  copy of the treatment parameters present in the memories,
  the measurements detected by its own sensors or sensing sources, and
  via the main control unit copy of the measurement signals acquired by the sensors or sensing sources associated to each slave control unit.

27. Method of checking according claim 20, further comprising:
  displaying on display means of the said dialysis machine a message indicating a malfunction of the said dialysis machine when the said alarm signal is detected.

* * * * *

UNITED STATES PATENT AND TRADEMARK OFFICE
CERTIFICATE OF CORRECTION

PATENT NO. : 6,811,707 B2
DATED : November 2, 2004
INVENTOR(S) : Rovatti et al.

It is certified that error appears in the above-identified patent and that said Letters Patent is hereby corrected as shown below:

Column 6,
Line 12, "detected;" should read -- detected --.

Column 8,
Line 27, "means;" should read -- means, --.

Column 9,
Line 2, "means;" should read -- means, --.

Signed and Sealed this

First Day of February, 2005

JON W. DUDAS
*Director of the United States Patent and Trademark Office*